United States Patent [19]

Barbanell

[11] Patent Number: 5,138,468
[45] Date of Patent: Aug. 11, 1992

[54] KEYLESS HOLOGRAPHIC LOCK
[75] Inventor: Joseph Barbanell, Concord, Calif.
[73] Assignee: DZ Company, Concord, Calif.
[21] Appl. No.: 473,890
[22] Filed: Feb. 2, 1990
[51] Int. Cl.⁵ .............................. G06K 9/00; G06K 9/76
[52] U.S. Cl. ............................................. 359/2; 235/457;
356/71; 359/29; 359/561; 359/564; 382/4;
382/31
[58] Field of Search ................... 350/162.13, 162.14,
350/3.6, 3.68, 3.75, 3.77; 382/2, 3, 4, 5, 31;
235/380, 382, 454, 457; 356/71; 359/2, 29, 561,
564

[56] References Cited

U.S. PATENT DOCUMENTS

| | | |
|---|---|---|
| 2,936,607 | 5/1960 | Nielsen . |
| 3,383,657 | 5/1968 | Claassen et al. . |
| 3,483,513 | 12/1969 | Burckhardt et al. . |
| 3,622,988 | 11/1971 | Caulfield et al. . |
| 3,643,216 | 2/1972 | Greenaway et al. .................. 382/2 |
| 3,716,301 | 2/1973 | Caulfield et al. . |
| 3,776,616 | 12/1973 | Douklias . |
| 3,819,911 | 6/1974 | Greenaway ............................. 382/2 |
| 3,928,842 | 12/1975 | Green et al. ............................ 382/4 |
| 3,944,978 | 3/1976 | Jensen et al. ................... 350/162.13 |
| 4,053,228 | 10/1977 | Schiller . |
| 4,213,038 | 7/1980 | Silverman et al. .................. 235/382 |
| 4,227,805 | 10/1980 | Schiller . |
| 4,303,852 | 12/1981 | Silverman et al. .................. 235/458 |
| 4,385,831 | 5/1983 | Ruell . |
| 4,428,670 | 1/1984 | Ruell et al. . |
| 4,429,413 | 1/1984 | Edwards . |
| 4,455,083 | 6/1984 | Elmes . |
| 4,532,508 | 7/1985 | Ruell . |
| 4,641,350 | 2/1987 | Bunn . |
| 4,684,801 | 8/1987 | Carroll et al. . |
| 4,684,802 | 8/1987 | Hakenewerth et al. . |
| 4,729,128 | 3/1988 | Grimes et al. ....................... 235/380 |
| 4,785,171 | 11/1988 | Dowling, Jr. et al. . |
| 4,876,725 | 10/1989 | Tomko ................................... 382/2 |

Primary Examiner—Bruce Y. Arnold
Assistant Examiner—Martin Lerner
Attorney, Agent, or Firm—Limbach & Limbach

[57] ABSTRACT

A keyless holographic locking device that uses a matched optical filter to store in form of a hologram a unique identificaton such as a fingerprint of an authorized user, a source of coherent light that provides the illumination, and an input element for providing angle-invariance possessing the form of a transparent window against which the user places and rotates the same fingerprint, and a registering device for registering the correlation optical signal between the stored fingerprint and the presented fingerprint to generate a signal to unlock the device when, and only if, a positive correlation exists between the presented and the stored fingerprints. A keyless two-stage holographic locking device, using a generalized matched optical filter wherein additional information for authorization is stored in a reference beam during the preparation of said filter, and wherein a second-stage optical correlation is also performed to register a second correlation between the stored additional information and a second identification presented by the user.

11 Claims, 4 Drawing Sheets

KEYLESS HOLOGRAPHIC LOCK

FIELD OF THE INVENTION

This invention relates in general to keyless locking devices and in particular to an automatic and keyless holographic locking device which utilizes known coherent pattern recognition techniques.

BACKGROUND OF THE INVENTION

Pattern recognition systems have been proposed in which stored reference images are correlated with input images.

For example, U.S. Pat. No. 3,716,301, issued Feb. 13, 1973, to Caulfield, et al., describes a fingerprint identification apparatus in which a user presses a finger against an input prism (prism 14), and a laser beam is reflected from the input prism's surface to generate an input image representing the Fourier transform of the finger image. The input image is then correlated with a reference image having been recorded in an already prepared hologram of the said transform. At column 5, lines 57-62, Caulfield, et al. teach use of a mechanically rotating dove prism to compensate for misalignment of the user's finger with respect to the input prism. At column 7, lines 28-66, Caulfield, et al. also teach use of a prerecorded Fourier transform hologram representing two or more reference images (each having a different rotational orientation) and presentation by the user of two different input images (each having a different orientation).

U.S. Pat. No. 4,227,805, issued Oct. 14, 1980, to Schiller, describes another pattern recognition system. In the system of U.S. Pat. No. 4,227,805, the user's finger rests in a linearly translatable carriage (carriage 20), and is scanned by a laser beam as the carriage translates linearly. The laser beam is reflected from a surface of the carriage, and the reflected beam is passed through a lens to generate an input image representing the Fourier transform of the finger image. The input image is then correlated with a reference image as it propagates through a prerecorded Fourier transform hologram (hologram 34).

However, the use of mechanically moving components in conventional correlation systems (such as the rotating Dove prism of U.S. Pat. No. 3,716,301, and the translating carriage of U.S. Pat. No. 4,227,805) undesirably causes noise due to vibration of the moving components. Furthermore, the mechanical motion is undesirably slow, so that scanning time required for producing a single correlation signal is undesirably long.

It has been proposed that pattern recognition systems of the correlation type be employed in lock devices. For example, U.S. Pat. No. 2,936,607, issued May 17, 1960, discloses a lock apparatus in which a user's fingerprint is electronically correlated with a stored reference fingerprint image.

However, it has not been known until the present invention how to design or operate a holographic locking device in which an input image is correlated in real time with an already prepared Fourier transform hologram (representing a single reference image), without employing mechanically moving components. Nor has it been known how to implement a two-stage holographic locking device in which correlation between two input images and two prerecorded reference images is performed rapidly and accurately in order to open a lock, and which does not employ moving mechanical parts.

SUMMARY OF THE INVENTION

The primary object of the present invention is to provide a locking device with an input element that utilizes a real-time angular-invariant unique identification of an authorized user, such as a fingerprint or other unique identification, to open the lock.

A further object of the invention is to provide a holographic lock which utilizes a particular fingerprint of an authorized user stored in the form of a hologram that is optically continuously compared to a presented rotating fingerprint and which authorizes unlocking of the device only when the presented fingerprint correlates with the stored fingerprint.

A further object of the invention is to provide an automatic and keyless holographic locking device in which the stored fingerprint of the authorized user may be readily changed by the user.

A further object of the invention is to provide, in one embodiment, double authentication, such as a first level requiring the fingerprint of the authorized user and a second level requiring the signature of the authorized user, before the locking device will be activated.

Further objects and advantages of the invention will become apparent from the following description and the drawings.

DETAILED DESCRIPTION

Figure 1:
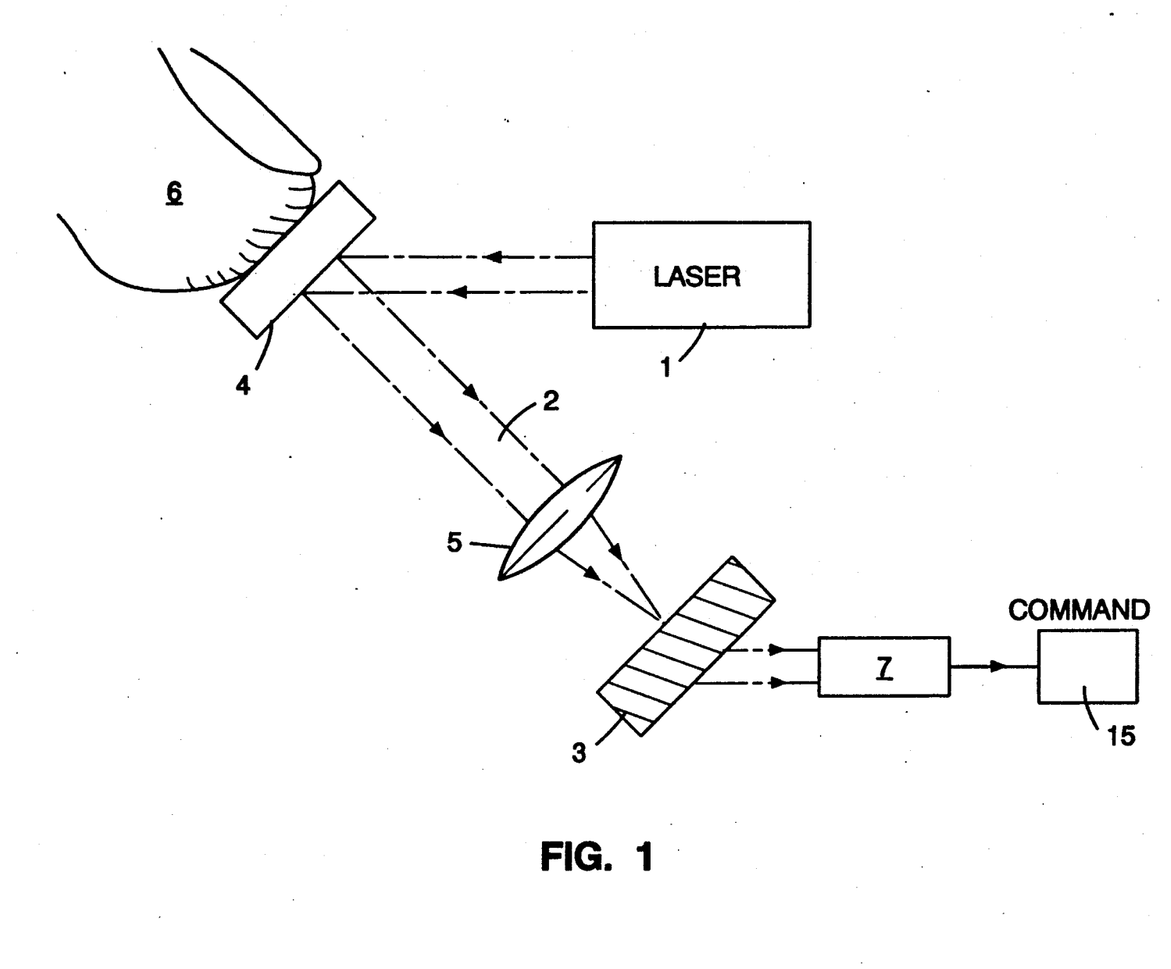
FIG. 1 is a schematic representation of a locking system according to the present invention.

The locking device shown in FIG. 1 may include any sort of mechanical, electronic or pneumatic lock control 15 which operates in response to a command signal from photoelectric element 7. The system includes a source of coherent light, such as for example a laser 1. In a low cost implementation, the source of coherent light for the authentication step may be a source of partially coherent light such as a neon lamp. (During the step of storing a reference fingerprint holographically, a laser light-source should always be used.) Thus the phrase "coherent light-source" is used here to denote both sources of completely coherent light and sources of partially coherent light. Use of a laser provides a very small probability of error at a significant cost compared to a neon lamp but is justified in many applications of the invention by the said probability of error.

The usage of Fourier transforms (and not the images themselves) is fully justified and not discussed here, as the practice is already approved and widely realized in the numerous applications of pattern recognition techniques. Among the advantages of use of Fourier transforms is the invariance of the in-plane filter's orientation. Also, when using the Fourier transform of such an informative object as a fingerprint, only about 1% of the initial fingerprint is needed for assured recognition.

Procedures under discussion are utilized in coherent pattern recognition techniques, but in all the applications of the latter, the main problem is that the accuracy is dependent on the placement of the matched filter (or on the relative orientation of the input object and corresponding matched filter).

The recognition system (lock) of the invention is very sensitive to the relative angular orientation of the matched filter and the object under recognition, i.e., the fingerprint of the user.

This produces the main and biggest problem to the real-time automatic recognition of all the existing optical pattern recognition systems. In the claimed system (lock) the inventor deals with the named problem in the most simple and efficient way.

To realize this procedure in the simplest way the inventive system includes an input element in the form of a transparent window 4. This element makes it possible to overcome the main disadvantages of prior similar systems by providing a means for the real-time angular orientation that makes the system functional in real-time. Against this element 4 the user places the tip of a particular finger 6 for identification purposes and, optionally, to activate the light source 1.

The light from the source 1 illuminates fingertip 6, and the light reflected from the fingertip passes as an encoded beam 2 through the spherical lens 5 which projects said beam upon the matched filter 3, located at its shadow plane. Matched filter 3 represents the complex spatial Fourier transform of the image of a reference (authorized) fingerprint, having been produced with coherent light on any suitable recording medium such as photographic, thermoplastic or photothermoplastic media.

In use, the user rotates the fingertip 6 in order to align the Fourier-transform of the introduced fingerprint with the stored holographic representation of the authorized fingerprint in matched filter 3, and in that way to eliminate the main, mentioned disadvantage of prior art systems.

As the user rotates fingertip 6 correlation procedures are realized continuously in time until the images are angularly matched and a correlation signal is present.

The Fourier-spectrum comparison provides invariance to in-plane displacements (i.e., displacements in the plane of window 4's surface) of the introduced image and invariance to in-plane scale differences. The chosen procedure provides automatically the formation of the correlation signal inside of the wavefront, the procedure being absolutely real-time, as a result of the implementation of the two-dimensional spatial comparison.

Two additional sources of displacement errors are treated as follows.

The correlation signal is greatly dependent on in-focal orientation of the matched filter 3. This problem is avoided by fitting the filter exactly in the back focal plane of lens 5 in the lock. That can be easily achieved by different methods. Two of them are as follows:

(a) The pre-prepared filter is fitted into the lock, and the entire device is afterwards produced like solid state optics (being, for instance, melted with transparent plastic);

(b) The system being optically reversible, the lock of the invention itself is used for filter preparation.

The linear shifts (misplacements) of the matched filter in the back focal plane of the lens 5 absolutely do not affect the recognition procedure.

In the shadow plane of the matched filter 3 a photosensitive element 7 is located. Its output command signal is connected to lock control 15 (mechanical, electronic or pneumatic) which unlocks the device.

For further functional improvement the device of the invention may additionally include a second spherical lens (not shown) which is situated in such a way that the matched filter is in the front focal plane and the photodetector is in the rear focal plane of said lens correspondingly. The function of said lens is to focus the signal of correlation, if any, on the surface of photodetector 7.

The correlation signal's orientation in the plane of photodetector 7 is unambiguously defined by the angular orientation of the reference beam (to be discussed below with reference to FIG. 3) during the stage of matched-filter preparation. The correlation optical signal, if any, appears in the exact geometrical point of the plane of photodetector 7. This can additionally serve as a protective measure, keeping the angle of reference wave orientation secure. Thus the photoelement 7 can be located in the fixed position, and the optical part of the lock easily realized in solid-optics form.

Photoelement 7 serves the purpose of registering the formed correlation signal and generates an electrical output command signal when the correlation signal between the stored and introduced fingerprint is present. As the correlation signal in a single stage version of the inventive lock will always be a bright spot (plane reconstructed wave, or the Delta-function after additional focusing), it can be registered by simple photosensitive means.

In a recognition mode of operation, laser 1 is activated by pressing the user's finger against the transparent window 4. The reflected light beam 2, being modulated in amplitude by the user's fingerprint 6, passes through the spherical lens 5, which forms its complex Fourier spectrum in the plane of the matched optical filter 3. The user rotates his finger against transparent window 4, until the spectra coincide angularly. If the spectra additionally match, and only then, the correlation signal in the form of a bright spot appears on the surface of photodetector 7. The position of the named spot, if any, is unambiguously predetermined.

The process can be further refined by focusing the correlation signal. To achieve this a second focusing lens is added (not shown). It is situated in such a way that matched filter 3 is in its forward focal plane and photosensor 7 is in its rear focal plane. The said photosensitive element 7 then generates the command electrical signal as previously described.

By utilizing the user's fingerprint as the source of authentication, the probability of error is of the order of 1 in 10,000,000. The inventive device will still be functional even if only a small part of the fingerprint is presented.

The recognition procedure is a real-time one and can be realized with the speed of $10^{-8}$ second.

The present invention eliminates the main problem of similar prior devices, that is the extreme sensitivity of the system to the input fingerprint/filter relative angular orientation. This problem is solved by the chosen input element—a transparent window 4 against which the user rotates his finger. This causes the rotation of the corresponding spectrum in the plane of matched filter 3 until the position of angular coincidence is achieved. Then and only then may the correlation peak be formed.

Rotation of the input fingerprint can be formally represented as a sequence of separate recognition steps, each one being realized with practically unlimited speed. In other words, the user can rotate his finger with any speed he likes.

It should be noted that using self-developing registering media for the matched filter, the user himself, fully automatically, can prepare the needed filter using the claimed lock (as will be described below with reference to FIG. 2).

Such filter preparation procedures are discussed in detail in the theory of optical matched filtering. The thing to be emphasized is that the claimed lock can be produced in a user-modifiable form, the memory for matched filters being long-time, changeable and realized on reversible media optically.

Structurally this changeability can be realized by adding an optical switch which activates a reference beam during filter preparation. Such a switch can be connected to a knob on the outside of the lock's housing, with an instructional indication such as "prepare", for instance.

Using self-developing registering media and applying recognized techniques, the named procedure can be fully accomplished by the user himself. This is done by using the additions to the system shown in FIG. 2. In FIG. 2, optical switch 11 is activated in response to a user command (for example, when the user activates a knob, not shown, on the lock's housing). When activated, switch 11 diverts away from window 4 a portion of the light incident thereon from laser 1. Such diverted portion propagates toward element 3 as reference beam 12. The rest of the light from laser 1 (sometimes denoted herein as the "object beam") propagates through switch 11 to window 4, and thereafter from window 4 through lens 5 to the plane of filter 3.

Figure 2:
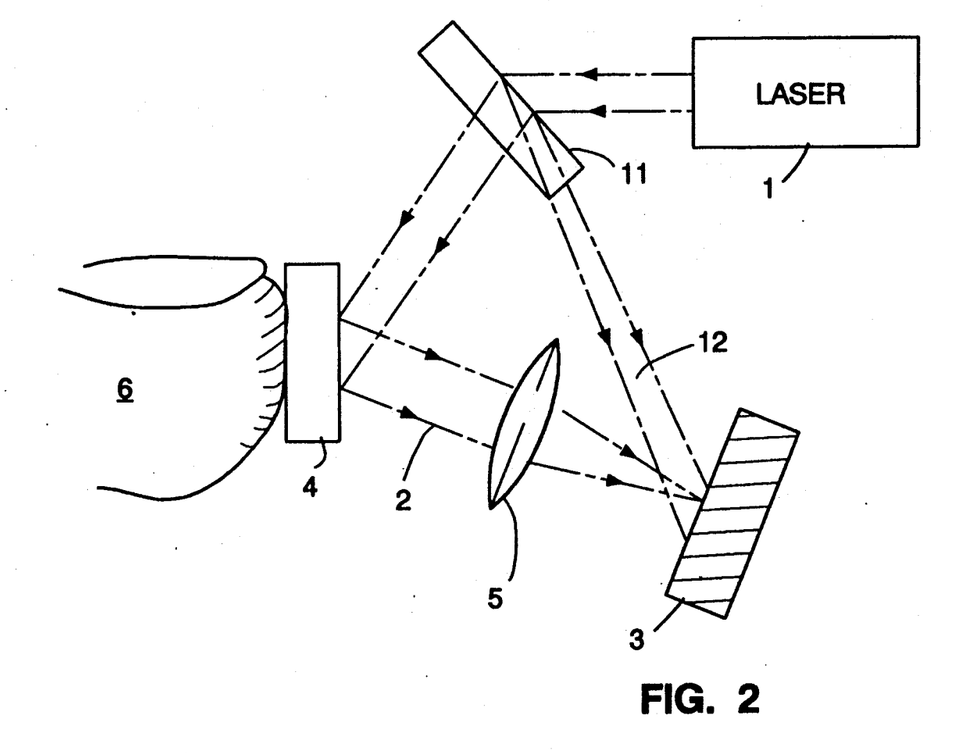
FIG. 2 is a schematic representation of another embodiment of the inventive locking system showing how the complex spatial Fourier transform of a fingerprint of an authorized user is registered by the user himself on a storage medium within the locking system.

In actual operation of the FIG. 2 system the user presses his fingerprint 6 onto the input window 4 of the lock, thus activating laser 1. (He receives confirmation that the laser has been activated by the illumination of input window 4). Then the user switches on the "prepare" knob (not shown), the reference beam 12 becomes activated, and the Fourier transform of his pressed finger is automatically implemented inside of the lock in the form of a matched optical filter (embodied in element 3). After the knob is switched off (to deactivate the reference beam), the lock is absolutely ready and prepared for recognition (approval) proceedings.

Though the verification procedures are absolutely foolproof from mistakes within the limits of any known approving devices (with the above-stated probability of errors), additional preventive measures can be easily suggested and incorporated. For standard consumer needs, though, the inventor does not suggest their implementation, as the locks become increasingly complicated and expensive.

For the modified locks, to be referred to as "two-stage" locks, the matched filter is prepared separately, the corresponding technique being very simple. In creating the two-stage lock, during the stage of matched filter preparation the so called "generalized hologram" technique is applied. That means that the reference beam includes an additional informational carrier, whether transmitting or reflecting. (For instance, additional information can be introduced by computer display, the reference laser beam being reflected from its surface).

By incorporating optical processing, said information can be of any degree of graphic complexity. The simplest but most representative case of including a codeword is discussed below. The latter is chosen by the inventor due to usual custom, for example the code word may be the signature of the user.

During the stage of matched filter preparation, the said signature of the user is included in the reference beam (by means of a slide transparency, from a computer display, etc.). Then after the first stage of recognition is concluded (i.e., fingerprints match), in the predetermined position in the place of photodetector 7 will appear not a bright spot, but the image of the chosen code word i.e., (the signature), having been previously included. (In this modification the additional focusing of the correlation signal is not needed).

Figure 3:
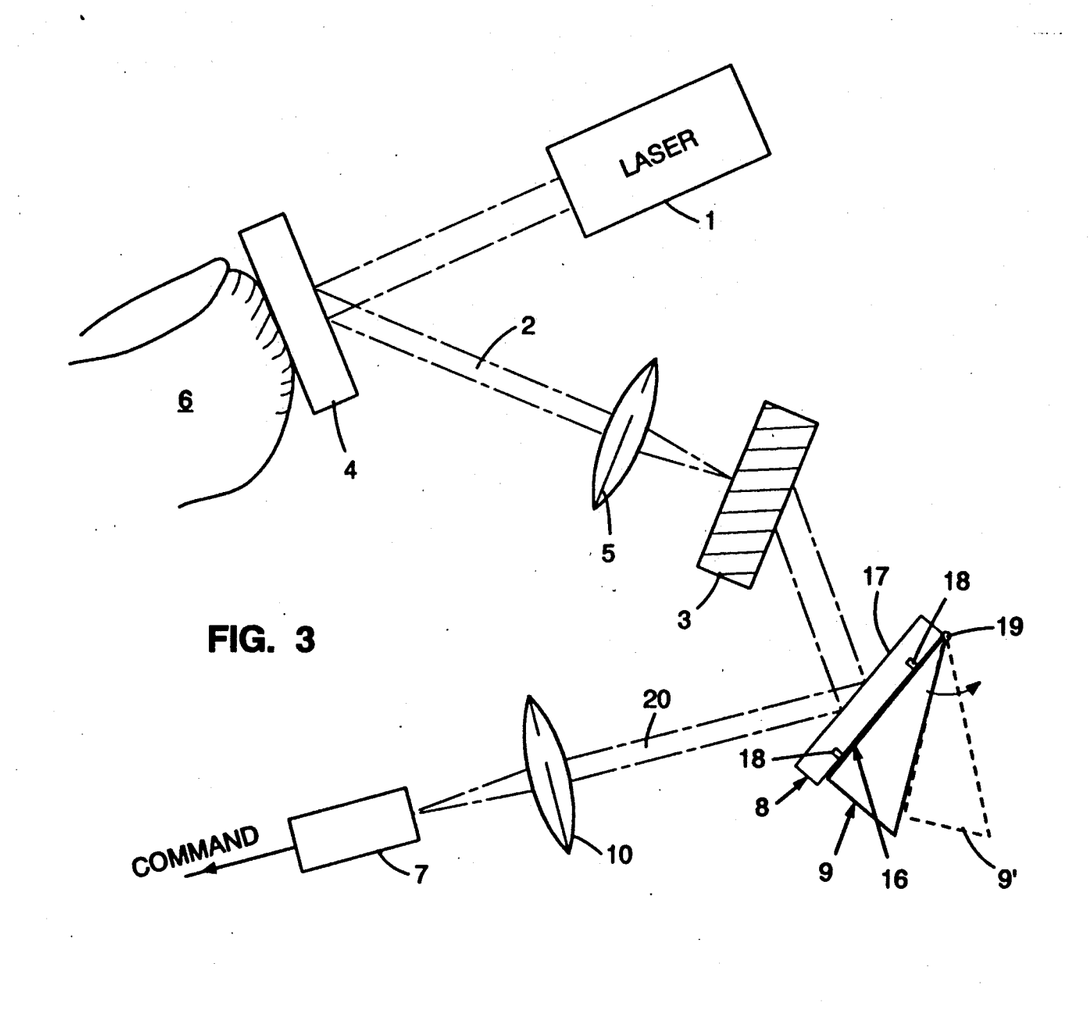
FIG. 3 illustrates schematically another embodiment of the inventive locking system which employs double authentication features.

To use fully the advantages of optical processing (no time lapse, no computerized elements), the approval of the signature itself in the two-stage modification of the claimed device could be also realized optically. An additional different stage of optical filtering is added in this embodiment (as shown in FIG. 3). The FIG. 3 embodiment includes: laser 1, "generalized" matched filter 3, input elements (transparent windows) 4 and 8, lenses 5 and 10, finger 6, photoelement 7 with output connected to the control device, and rotating lid 9.

In this modification (shown in FIG. 3), the lock additionally includes a second transparent window 8, being situated on the path beam 2. Window 8 possesses lines/grooves 18 for angular orientation of the additional graphic information (in this particular case, the signature of the user) presented at window 8 in relation to the in-plane orientation of matched filter 3.

To window 8 is attached movable lid 9. This lid, which may be rotated about pivot 19 relative to window 8, has a triangular cross-section and a mirrored inner surface 16. Following the input element 8, along the optical path of beam 2, standard spherical lens 10 is located. The angular space orientation of the latter's optical axis corresponds to the arbitrary (but fixed) angle of window 8. In the back focal plane of lens 10, on its optical axis, standard photoelement 7 is located.

The system of FIG. 3, using the generalized matched optical filter and applying the two-stage Fourier optical recognition procedure, functions in the following way.

In actual operation the user writes down his signature on the second input element 8 along (or between) the pre-positioned lines/grooves 18, then closes the lid 9 and presses his finger 6 to the window 4. The first stage of the recognition procedure is absolutely the same as in the single stage lock, having been described earlier. After the fingerprint is approved (and only in that case), an optical correlation signal is incident at inner plane 17 of window 8, causing the image of a pre-stored signature (previously stored in filter 3, together with information regarding the user's fingerprint) to appear on the inner plane 17 of window 8. It should be noted here that the angular orientation of the signature's reconstructed image depends on the orientation of the generalized matched optical filter 3 and is absolutely unaffected by the rotational movement of finger 6 during the first approval stage. After first stage approval, the pre-stored signature image (or, more generally, the second identification image exactly fits angularly the lines 18 on the second window 8. To provide assured recognition on the second stage, angular discrepancies within the range of 10 degrees are absolutely allowable.

The user may check that the first stage is finished (his fingerprint is approved) by opening the lid 9 (by rotating lid 9 about pivot 19 into position 9' shown in phantom view in FIG. 3) and checking to see if the image of his signature has appeared. After first stage approval, the correlation light beam ("optical correlation signal"), already carrying the information about the pre-stored signature, is reflected from the mirrored surface 16 of the lid 9 (when lid 9 is closed, as shown in FIG. 3, so that surface 16 abuts window 8).

In reflected beam 20 the image of the signature written down on second input element 8 is multiplicatively superimposed on the pre-stored image from the filter 3. After passing the lens 10, both images are correlated by their corresponding Fourier spectra on the surface of the photodetector 7.

Fourier spectrum comparison is chosen and implemented because its results are unaffected by the relative linear dimensions of the compared images: to be approved the pre-stored signature (in the generalized matched filter 3) and signature written on window 18 need not linearly match exactly. A very important feature of this structure is that during the second stage of approval, the corresponding images are multiplied and not added.

The most attractive feature of the two-stage lock of FIG. 3 is that all operations are performed by optical processing without involving electronic processing techniques of any level, thus excluding both the additional time-lapses and/or errors.

The described sophisticated two-staged locks are not intended for such applications as suitcases, wallets, etc., but can be useful in safes, apartment door locks, and other applications demanding a high level of security.

It should be noted that while using the generalized holographic filter, more elaborate information—analog or digital up to any degree of complexity—can be implemented. However, in all the lower level security applications the incorporation of more elaborate information is not needed. The suggested technique, especially the two-staged modification, already provides the needed level of security. Security applications requiring more elaborate sheltering information will additionally demand digital computerized processing. This would mean the repetition by optical procedures of already existing sheltering devices with memories on the standard information media—computers, magnetic/optical disc media, etc.

Figures 4, 5:
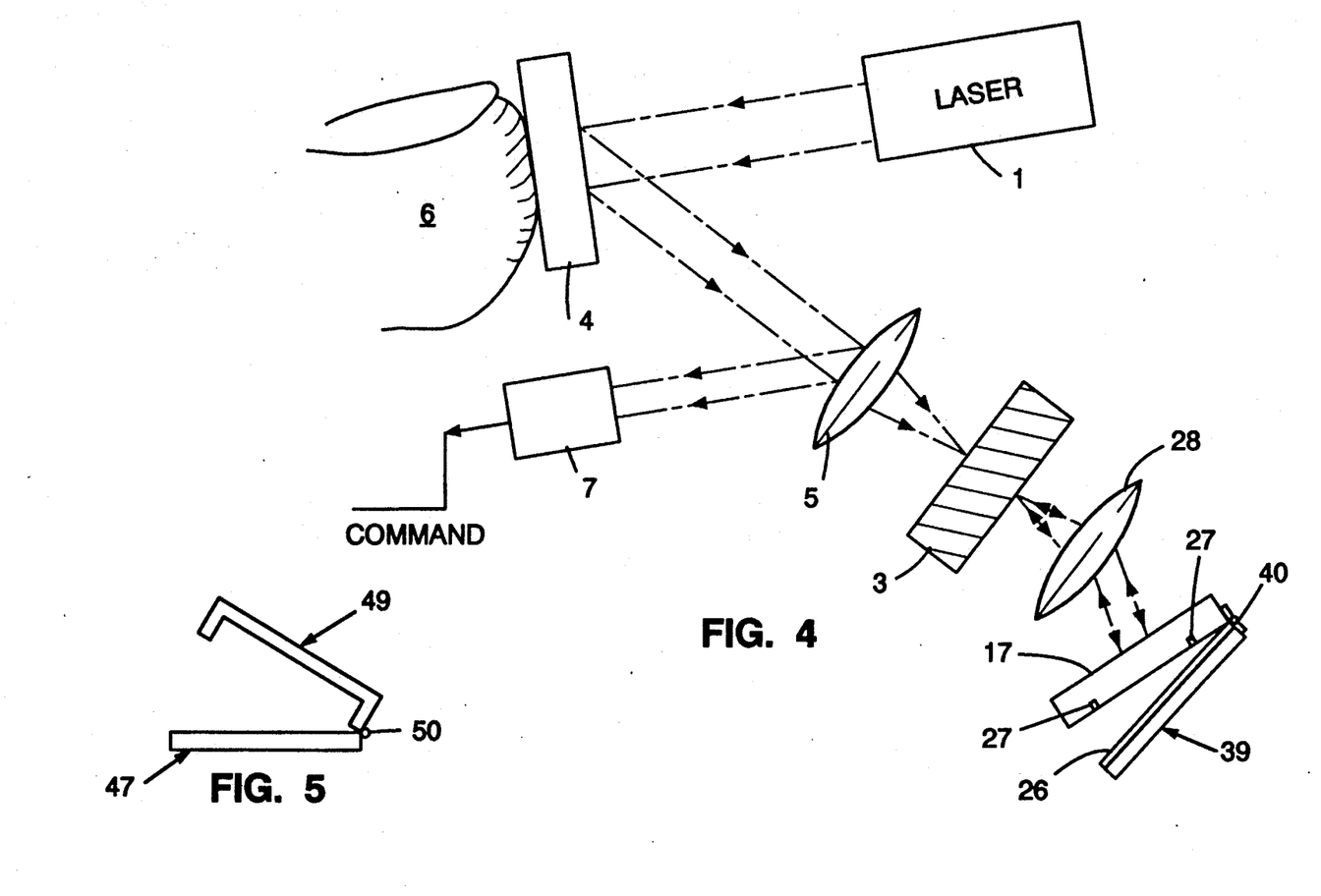
FIG. 4 is a schematic representation of yet another embodiment of the inventive locking system.
FIG. 5 is a side view of an embodiment of the inventive transparent window and mirrored rectangular lid.

A more sophisticated modification of the matched filter is being disclosed in order to perform both correlation steps in one embodiment, to exclude the second optical channel, and to greatly simplify the optical adjustment (without adding to the expense of the filter preparation). This filter and its functioning will next be described with reference to FIG. 4. In FIG. 4, components corresponding to those in FIG. 3 are identified by the same reference numerals as in FIG. 3. In FIG. 4, second window 17 is oriented so that when rotatable lid 39 is closed against it, the incoming beam from generalized matched filter 3 (through lens 28) is reflected back to generalized matched filter 3 (through lens 28). This permits implementation of a more compact and simple two-stage locking device.

The system of FIG. 4 performs the first stage of approval in the same manner as does the FIG. 3 system (with the sole difference that, in FIG. 4, the optical correlation signal from matched filter 3 is focused by lens 28 before reaching window 17). After multiplication with the second identification (which may be the user's signature) presented at window 17 between alignment grooves 27, the optical correlation signal is reversed optically back toward lens 28. Specifically, when flat lid 39 is rotated about hinge 40 so that inner mirrored surface 26 abuts window 17, the optical correlation signal will reflect from surface 26 back through window 17 to lens 28.

The reflected beam (from window 17 and lid 39) passes through lens 28, which forms its complex Fourier spectrum in the plane of generalized matched optical filter 3. In FIG. 4, filter 3 provides matched filtering on both stages of approval. Although filter 3 performs a greater number of functions in the FIG. 4 embodiment than in the FIG. 3 embodiment, this does not affect the filter's physical complexity or cost.

The operation of preparing matched filter 3 for use in the FIG. 4 embodiment (the step of prestoring the second identification) is the same as that described above with reference to FIG. 2, except to the extent that the presence of lens 28 on the return path of the optical correlation signal introduces special demands on the reference beam. Specifically, the reference beam should be Fourier-transformed during the filter preparation step. If so, the image of the second identification will be reconstructed when the beam passes through lens 28 (after propagating to lens 28 from window 4 through lens 5 and filter 3).

The filter preparation step should be performed in such a manner that generalized matched filter 3 includes the matched spatial filter for the squared second identification (rather than the second identification itself). The separation of the two filters is realized by introducing an additional spatial subcarrier, in a manner that will be apparent to those ordinarily skilled in the art. Preparation of matched filter 3 in this manner ensures additionally the required positioning of the second correlation peak in the output plane.

After reflecting from lid 39, the optical correlation signal propagates through lens 28, filter 3, and lens 5 to photoelectric element 7. Element 7 generates a command signal only if the correlation signal between the first pre-stored identification in matched filter 3 and identification 6 appears at window 4, and the correlation signal between the second pre-stored identification in matched filter 3 and the second identification (for example, user signature) appears at window 17.

In addition to its simplicity, an advantage of the FIG. 4 system is that it provides matched filtering procedures during the second identification stage.

The modified lock (described with reference to FIG. 4) decreases the probability of false recognition up to $10^{-14}$.

An alternative input device, useful for replacing the lidded window in either the FIG. 3 or FIG. 4 embodiment, will next be described with reference to FIG. 5. In FIG. 5, hollow rectangular lid 49 is rotatably connected to transparent window 47 by pivot 50. The inner surface of lid 49, which faces window 47, is mirrored. Use of the FIG. 5 assembly, instead of the window 17 and lid 39 assembly of FIG. 4 desirably reduces problems with parasitic diffraction.

What is claimed is:

1. A keyless angular-invariant holographic lock capable of producing a command signal when a user presents an identification to the lock, wherein for angular invariancy the lock comprises:

an input element, including a transparent window against which the user presents the identification and rotates it for angular alignment with a pre-stored identification previously stored in form of a Fourier-hologram;

a matched optical filter upon which the prestored unique identification is stored in the form of said Fourier-hologram;

a coherent light-source for illuminating said identification with a beam at said transparent window;

means for projecting upon said optical matched filter a reflected coherent beam from the window, said reflected coherent beam having been encoded by said identification at the window; and optical means for registering a correlation signal, wherein the correlation signal is formed during optical comparison of the pre-stored identification with the presented identification during rotation of the presented identification, and for generating the command signal only when the correlation signal is unambiguously present, wherein the correlation signal is a first-stage correlation signal, and further comprising:

a second transparent window upon which the user presents a second identification;

a lid, rotatably attached to said second window and possessing a mirrored layer;

means for pre-storing a second unique identification in said matched optical filter, wherein the matched optical filter is represented in the form of a generalized hologram; and means for registering a second-stage correlation optical signal formed in the process of comparing the first-stage correlation signal from the matched optical filter with the presented second identification, and for forming the command signal only when the second-stage correlation optical signal is unambiguously present.

2. The lock of claim 1, wherein the mirrored layer is an inner surface of the lid.

3. The lock of claim 2, wherein the inner surface is a hollow rectangular surface.

4. The lock of claim 1, including specifically aligned grooves, corresponding to said matched optical filter's in-plane orientation, on the second transparent window.

5. A keyless angular-invariant holographic lock capable of producing a command signal when a user presents an identification to the lock, wherein for angular invariancy the lock comprises:

an input element, including a transparent window against which the user presents the identification and rotates if for angular alignment with a pre-stored identification previously stored in form of a Fourier-hologram;

a matched optical filter upon which the prestored unique identification is stored in the form of said Fourier-hologram;

a coherent light-source for illuminating said identification with a beam at said transparent window;

means for projecting upon said optical matched filter a reflected coherent beam from the window, said reflected coherent beam having been encoded by said identification at the window; and optical means for registering a correlation signal, wherein the correlation signal is formed during optical comparison of the pre-stored identification with the presented identification during rotation of the presented identification, and for generating the command signal only when the correlation signal is unambiguously present, wherein the correlation signal is a first-stage correlation signal, and wherein the matched optical filter is produced in the form of a generalized hologram in which a second unique identification is pre-stored, and further comprising:

a second transparent window upon which the user presents a second identification;

a lid, rotatably attached to the second window and possessing a mirrored layer; and means for registering a second-stage correlation optical signal formed in the process of comparing the first-stage correlation signal from the matched optical filter with the presented second identification, and for forming the command signal only when the second-stage correlation optical signal is unambiguously present.

6. The lock of claim 5, also including:

a lens between the matched optical filter and the second window, wherein said lens forms the complex Fourier spectrum of light reflected from the lid in the plane of generalized matched optical filter.

7. The lock of claim 5, wherein the matched optical filter includes a spatially separated second matched spatial filter for the first-stage correlation signal.

8. The lock of claim 7, wherein the matched optical filter includes a specially chosen spatial subcarrier additionally providing the positioning of the resulting correlation signal, positioning of the components of the lock, and simplifying the structure and adjustment of the lock.

9. The lock of claim 7 or 8, wherein the second matched spatial filter corresponds to the square of the second unique identification.

10. A method of activating a locking device, comprising the steps of:

storing a unique identification in the form of a Fourier hologram indicative of a person authorized to activate said device, presenting an identification to a transparent window and varying the angular orientation of the identification as it is presented, reflecting a beam from the window during variation of the identification's angular orientation, so that the reflected beam is encoded by said presented identification and the reflected beam is projected onto the Fourier hologram, continuously in time comparing said reflected beam optically with said hologram, and generating a command signal when an optical correlation signal is present between the presented identification and said Fourier hologram, further comprising the steps of:

encoding a reference beam with the unique identification and with a second identification, and directing said encoded reference beam to a self-developing medium, thus forming a generalized matched optical filter in which the unique identification and the second identification are holographically stored; and illuminating a second transparent window with the optical correlation signal, but only in the case that the optical correlation signal is present, wherein the optical correlation signal is an optical signal which reconstructs the stored second identification.

11. The method of claim 10, also including the steps of:

introducing an additional user identification on the second transparent window;

closing a mirrored lid against the second transparent window; and generating the command signal only when a second correlation signal is present, wherein the second correlation signal is formed in the process of reflecting the optical correlation signal from the mirrored lid in the presence of the additional user identification.

* * * * *